United States Patent [19]

Evans, Jr. et al.

[11] Patent Number: 4,482,967
[45] Date of Patent: Nov. 13, 1984

[54] CONDUCTIVITY DETECTOR AND METHOD

[75] Inventors: Barton Evans, Jr., Menlo Park; James B. Stolz, Mountain View, both of Calif.

[73] Assignee: Dionex Corporation, Sunnyvale, Calif.

[21] Appl. No.: 303,546

[22] Filed: Sep. 18, 1981

[51] Int. Cl.³ .................... G06F 15/42; G06F 11/00; G01N 27/46
[52] U.S. Cl. .................... 364/499; 364/571; 364/556; 364/496
[58] Field of Search ............... 364/482, 496, 499, 571, 364/497, 550, 556, 554, 580; 73/23, 23.1, 26

[56] References Cited

U.S. PATENT DOCUMENTS

| | | | |
|---|---|---|---|
| 3,681,025 | 8/1972 | Dalgaard | 364/482 |
| 3,807,860 | 4/1974 | Brainard | 364/497 |
| 3,889,255 | 6/1975 | Pettersen | 364/499 |
| 4,063,447 | 12/1977 | Mathison | 364/571 |
| 4,159,523 | 6/1979 | Neer | 364/497 |
| 4,189,778 | 2/1980 | Vogel | 364/482 |
| 4,218,746 | 8/1980 | Koshiishi | 364/571 |
| 4,342,089 | 7/1982 | Hall | 364/571 |
| 4,357,668 | 11/1982 | Schwartz et al. | 364/497 |
| 4,368,509 | 1/1983 | Li | 364/497 |

OTHER PUBLICATIONS

'A Micro-Computer System for Potentiometric Stripping Analysis', by Anfält et al., Analytica Chimica Acta, 103, No. 4, (1978), pp. 379-388, (Elsevier Sci. Pub. Co., Amsterdam, Netherlands).
'Microprocessor-Controlled Differential Titrator', by Busch et al., Analytical Chemistry, vol. 50, No. 14, (1978).

Primary Examiner—Jerry Smith
Assistant Examiner—William G. Niessen
Attorney, Agent, or Firm—Flehr, Hohbach, Test, Albritton & Herbert

[57] ABSTRACT

Disclosed is a conductivity detector for use in chromatography systems. The improved conductivity detector provides digital processing of a conductivity signal to provide improved stability. The detector compares a trial offset signal with a detected conductivity signal and when the compared values are within a predetermined value the detector processes the compared value and the final offset value thereby providing improved accuracy with higher resolution.

8 Claims, 13 Drawing Figures

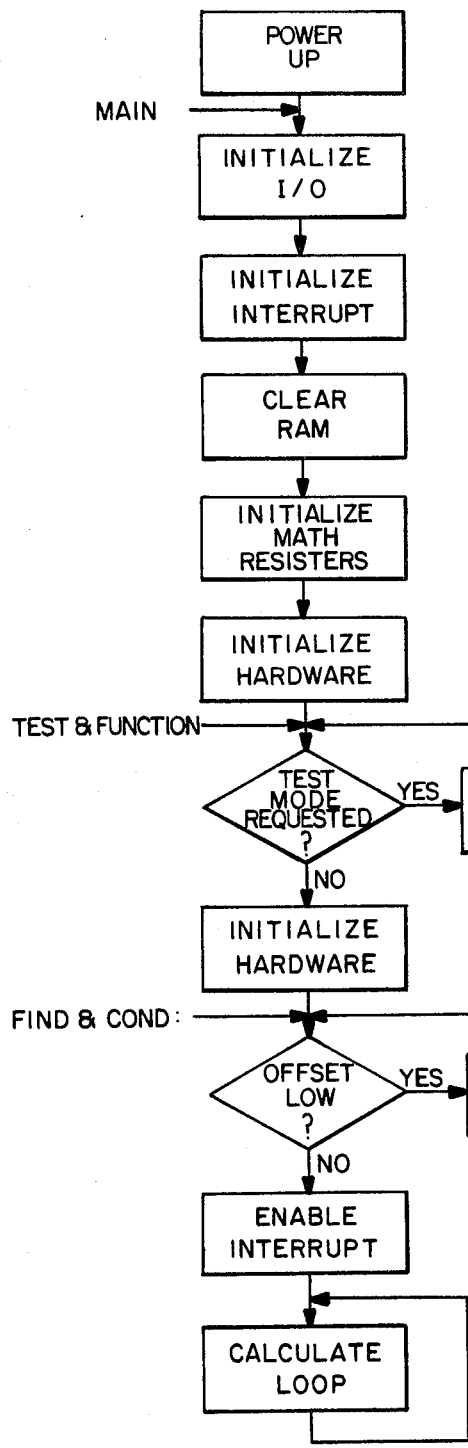
FIG.—1a
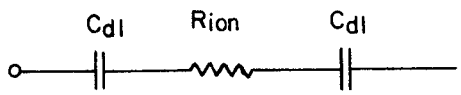
FIG.—1b
FIG.—1c
FIG.—4

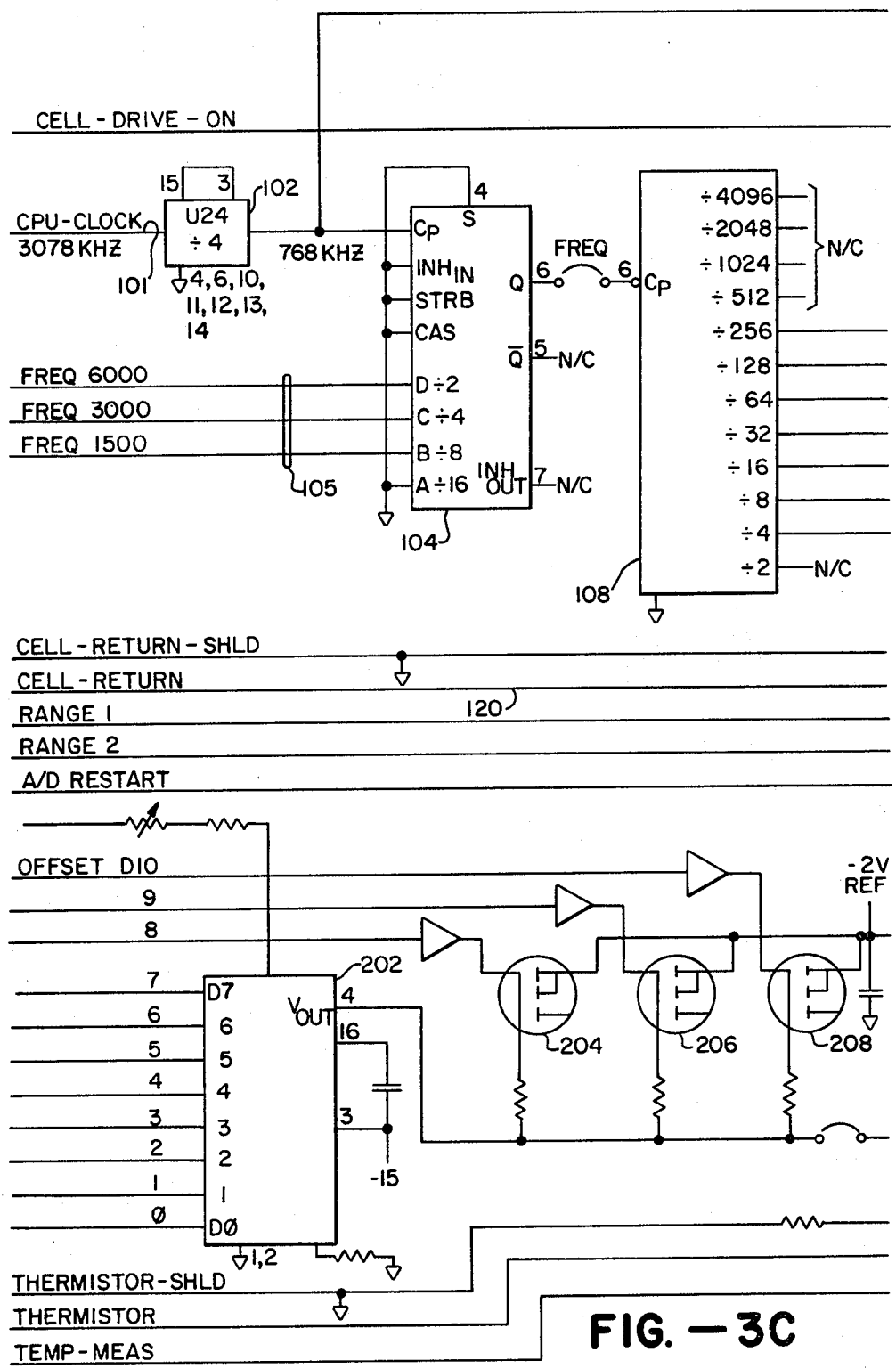
FIG. —3C

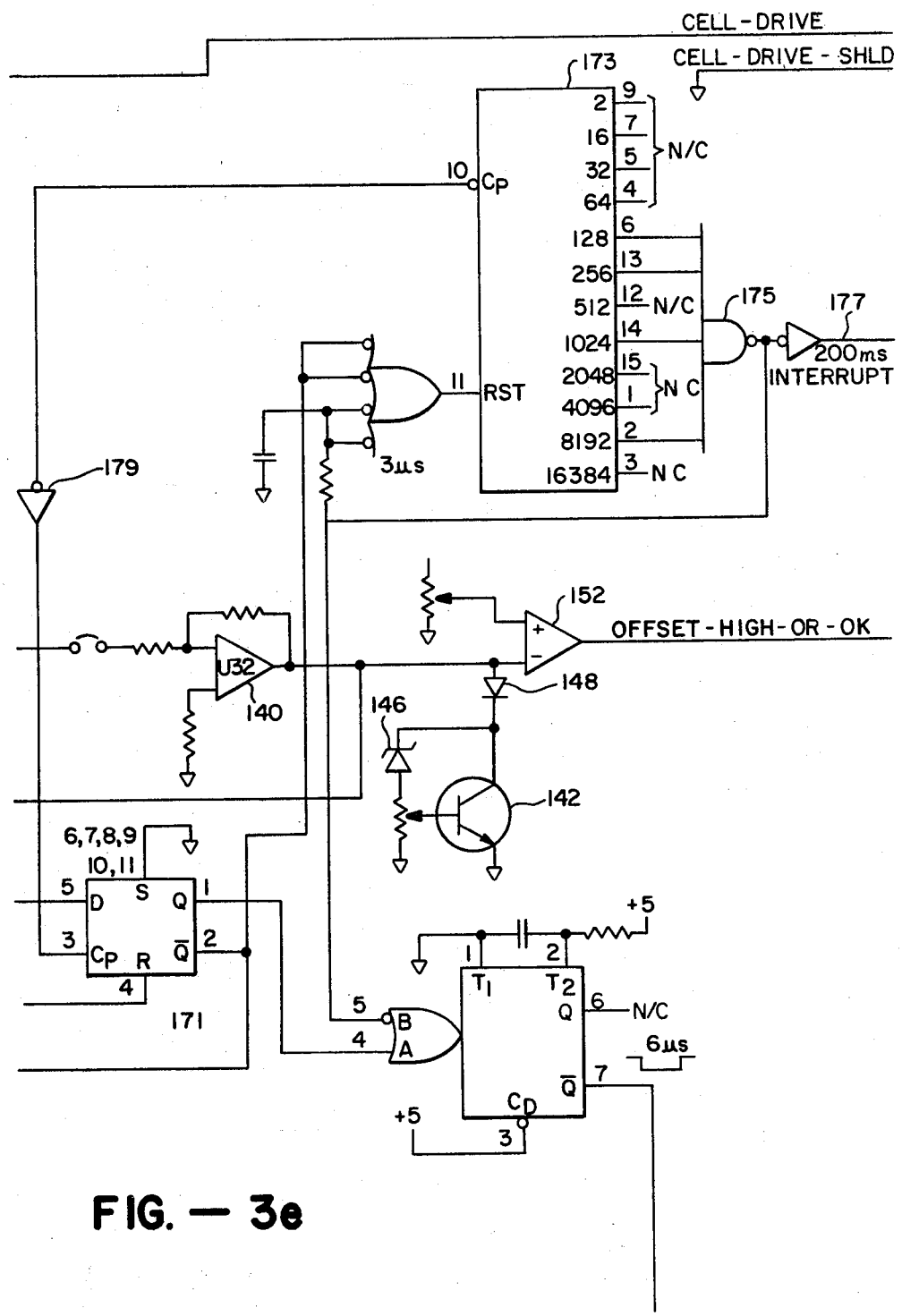
FIG. — 3e

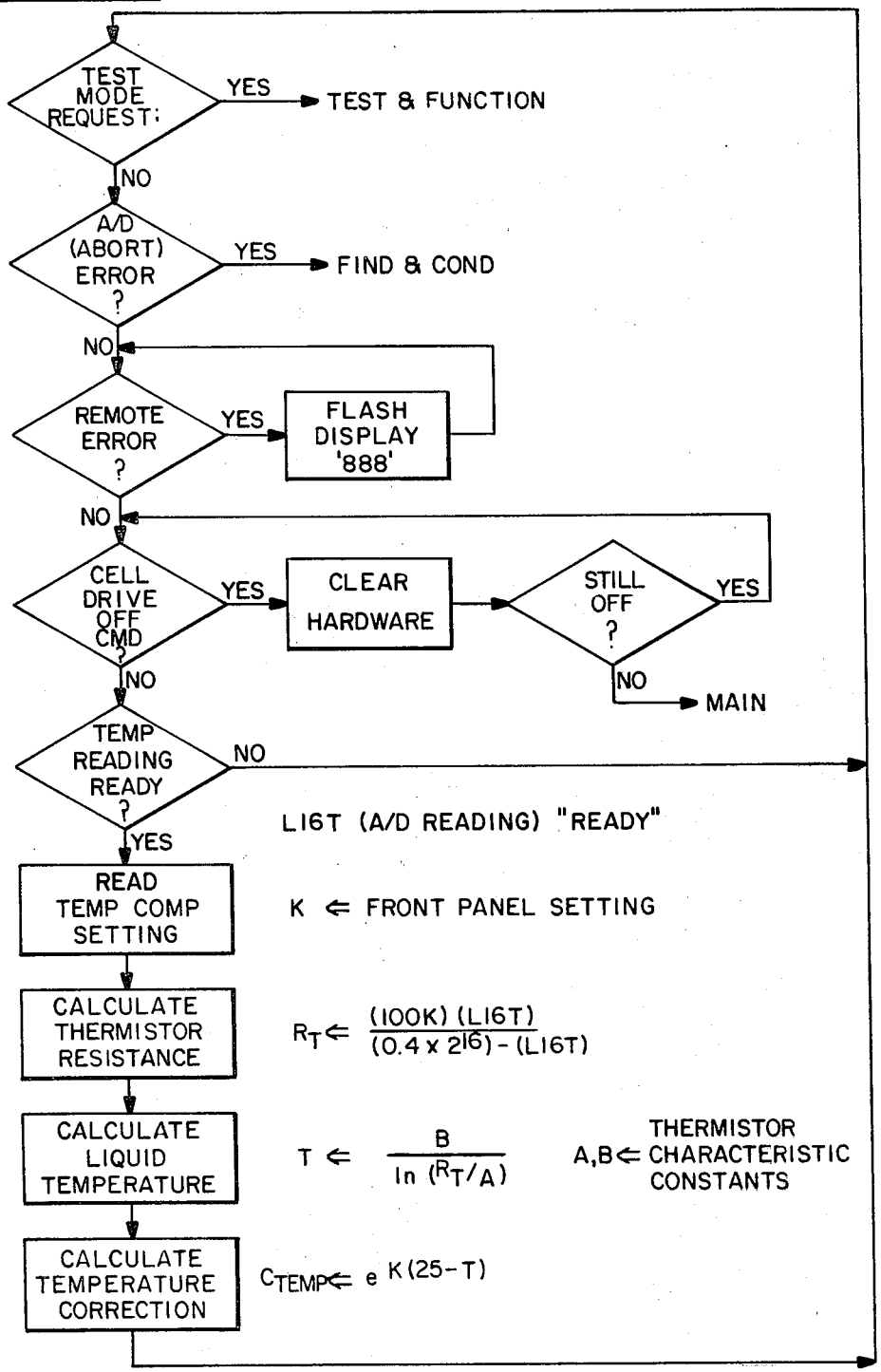
FIG.—5

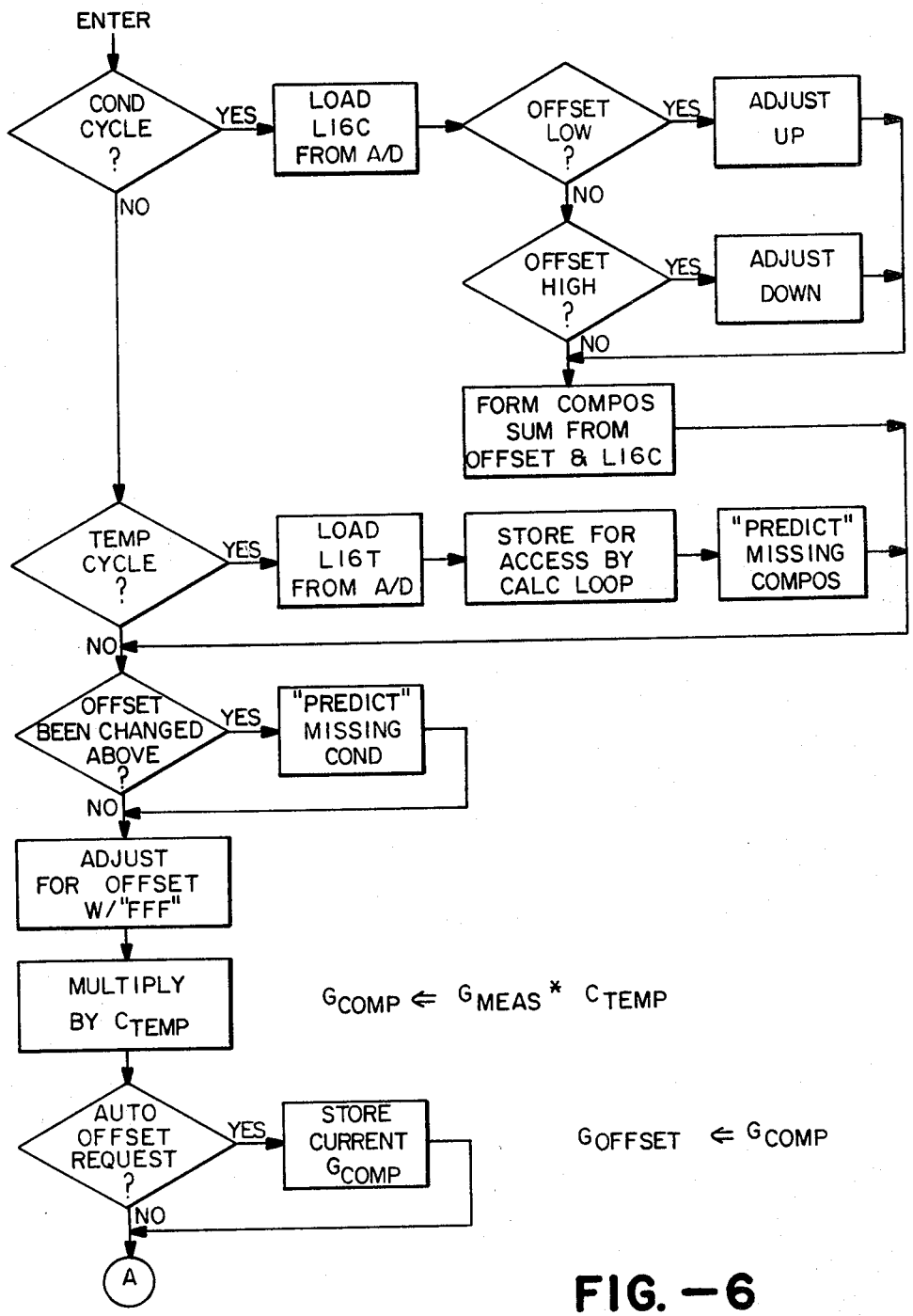
FIG.—6

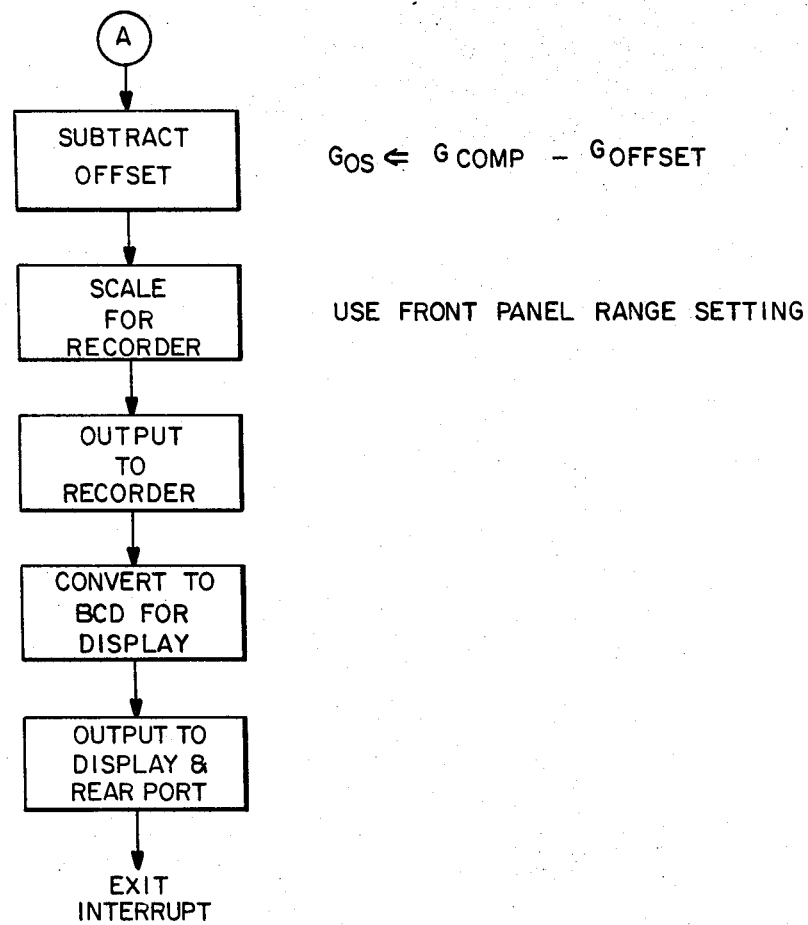
FIG. — 7

CONDUCTIVITY DETECTOR AND METHOD

BACKGROUND OF THE INVENTION

The present invention relates to a conductivity detector for use in chromatography systems.

Prior art conductivity detectors are utilized with chromatography systems in which a chemical solution passing through a chromatographic column to a liquid conduit is connected to a conductivity cell. Fluctuations in ionic concentration in the conductivity cell produce an electrical signal proportional to the amount of ionic material, which is detected by a conductivity meter. The detected electrical signal is in turn generally connected to a display means such as a chart recorder which provides a visible display to a user.

Prior art conductivity detectors have in general been deficient for use as laboratory grade instruments because of poor absolute accuracy and poor linearity. Because conductivity cells do not have a constant current vs. conductance relationship, prior art detectors have not in general been able to compensate for this non-linearity. In addition, prior art detectors are not capable of completely nulling out non-linear capacitive components of the chemical solution to be measured. In order to reduce the effects of solution temperature variation on a detector's baseline, it would be desirble for a conductivity detector to correct a measured conductivity to what conductivity would be at some fixed temperature (say 25° C.) so that output baseline is independent of changes in solution temperature.

Prior art detectors attempt to correct for temperature changes using thermistors, but are limited such that it is sometimes worse than no correction at all. This is because thermistor temperature is mainly affected by the cell body temperature due to poor thermistor positioning, the thermistor response is relatively slow (typically greater than thirty seconds) and the detector correction circuitry does not follow correct exponential relationships. Prior art detectors typically use a thermistor in a feedback loop of an operational amplifier so that the correction only approaches an exponential over a very limited temperature range.

In view of the above background, it is an objective of the present invention to provide an improved conductivity detector for use in chromatography systems.

SUMMARY OF THE INVENTION

The present invention relates to a conductivity detector and method for use in chromatography systems.

The conductivity detector includes means for processing a conductivity signal from a conductivity cell, including means for generating a trial offset signal and means for comparing the trial offset signal with a detected conductivity signal from a conductivity cell. If the compared signals are less than a predetermined value, the conductivity detector continuously increases the offset signal until the compared values are within a predetermined range. Thereupon the compared signal is converted to a digital format, typically 16 bits of resolution. The conductivity detector thus has the final value of the offset signal in digital format, typically 11 bits of resolution in one embodiment, and the compared difference value.

In this way, the conductivity is processed by the present invention with, in one embodiment, 11 bits of offset plus 16 bits of the compared value, or a total of 27 bits of resolution. This high resolution allows the present invention to operate with a low level of electronics-generated noise while providing reliable measurement of the actual conductivity.

In accordance with the foregoing summary, the present invention achieves the objective of providing an improved conductivity detector for use with chromatography systems.

Other objects and features of the present invention will become apparent from the following detailed description when taken in conjunction with the accompanying drawings.

BRIEF DESCRIPTION OF THE DRAWINGS

FIG. 1A depicts a timing diagram for a bipolar pulse waveform.

FIG. 1B depicts a schematic representation of a simplified equivalent circuit of a conducting electrolyte in a conductivity cell.

FIG. 1C depicts a schematic representation of the charging and discharging of the equivalent circuit of FIG. 1B.

FIGS. 3A-3E depict a more detailed diagram of the conductivity detector of FIG. 2.

FIGS. 4-7 depict flow charts for illustrating the operation of the conductivity detector of FIG. 2.

DESCRIPTION OF THE PREFERRED EMBODIMENT

In order to provide processing capability of a conductivity signal from a conductivity cell, the present invention utilizes fixed amplitude variable frequency bipolar-pulse cell drive as depicted in FIG. 1A, which, as will be described, cures the measurement accuracy problem described above, in which inherent cell non-linearity is compensated for by the improved conductivity detector.

The type of cell drive used by the present detector is, as shown in FIG. 1A, a bipolar pulse having a duration of positive then negative potential, followed by a long period during which the cell is effectively shorted out at zero potential. To understand why the scheme is superior in providing measurement accuracy and linearity, consider a simplified equivalent circuit of a conducting electrolyte in a conductivity cell as depicted in FIG. 1B, where $C_{dl}$=double layer capacitance due to the buildup of ions near electrodes, and $R_{ion}$ is the effective resistance from slow ionic drift. $C_{dl}$ is a major source of inaccurate and non-linear measurements. By utilizing a bipolar cell drive, this capacitance is charged up to a certain amount during the first potential then discharged exactly the same amount during the opposite potential cell drive, as depicted in FIG. 1C. At the end of this opposite potential the capacitor has zero charge (zero voltage) and at that instant the cell current is measured. Since the capacitor voltage is zero at this time, only the resistive component $R_{ion}$ of FIG. 1B is actually measured, which is the desired result. The conductivity cell is then shorted for a relatively long time to allow the ionic charge to equilibrate before another measurement.

Figure 2:
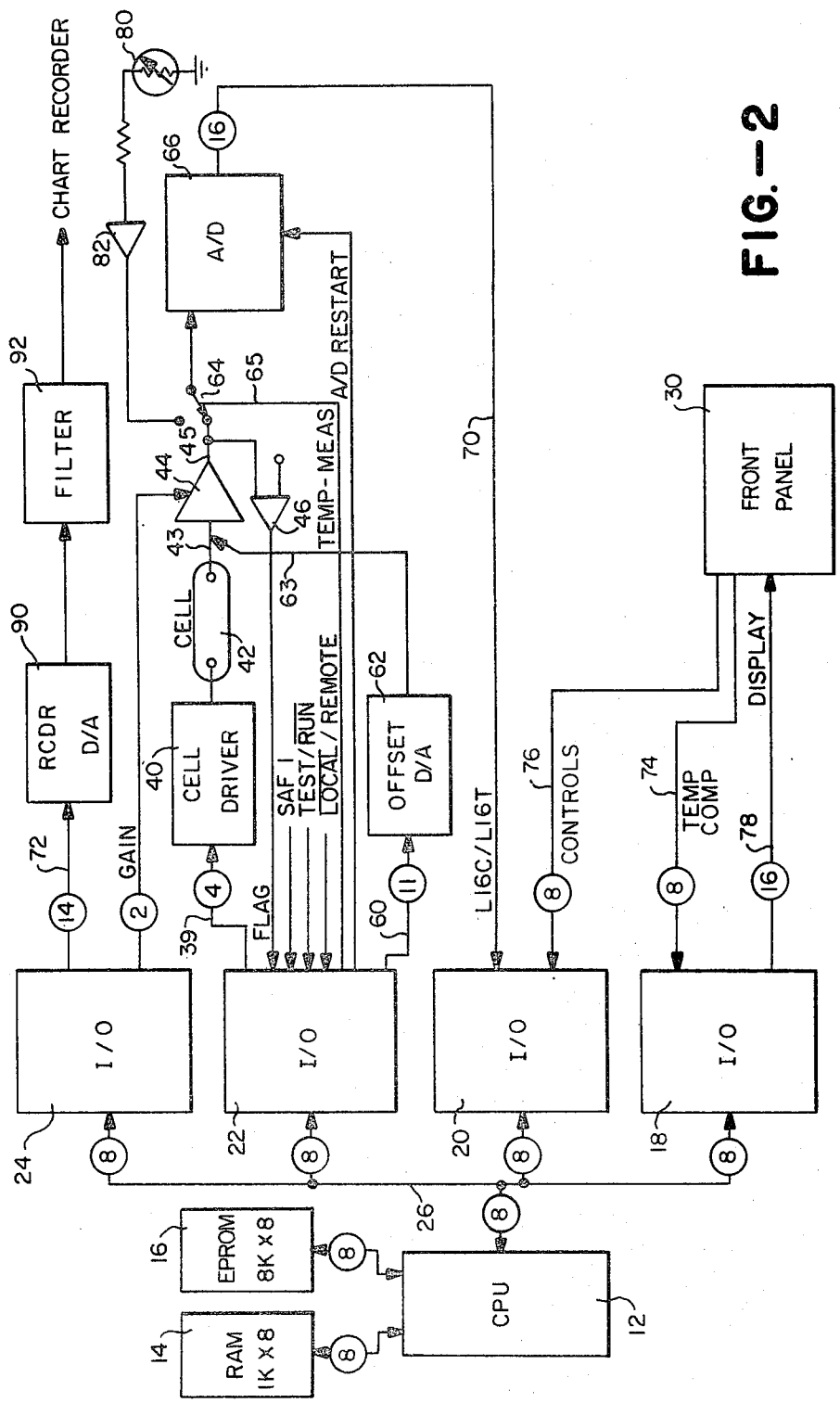
FIG. 2 depicts a block diagram of an improved conductivity detector according to the present invention.

Referring now to FIG. 2, a functional block diagram of an improved conductivity detector 10 according to the present invention is depicted.

In FIG. 2, the conductivity detector 10 includes a microcomputer 12, typically an Intel 8085 based system which includes 8085 CPU 12, RAM 14, EPROM 16, and input/output (I/O) circuits 18, 20, 22 and 24, all of which are typically on a single printed circuit board (PCB). In one embodiment, the conductivity detector 10 provides twelve 8-bit I/O ports. CPU 12 operates at 3.072 MHz, and this same clock is divided down and used for timing for the rest of the system.

Commands from a front Panel 30 (or if remote operation, from a rear panel parallel input) are processed and supplied to CPU 12 through I/O circuits 18, 20. These inputs tell the system what range has been commanded (part of bus 76), what special on/off bits have been commanded (part of bus 76), and what temperature coefficient (bus 74) has been selected. The outputs from CPU 12 are auto-ranged conductivity (in BCD format) out of I/O 18 to front panel display 30 through bus 78.

In FIG. 2, a cell drive signal is applied by cell driver 40 to a conductivity cell 42 in bipolar pulse format, as depicted in FIG. 1A, with ±2.5 volts peak and either 1.5 KHz, 3.0 KHz or 6 KHz, depending upon the range (higher frequencies are used for higher conductivities). A 4-bit signal on bus 39 applied to cell driver 40 selects the appropriate cell drive frequency for application to conductivity cell 42.

An 11-bit signal on bus 60 is applied from I/O circuit 22 to offset generator 62, an 11-bit D/A converter which generates an analog offset current signal on lead 63.

The current signal on lead 43 from conductivity cell 42 has the initial offset current on lead 63 subtracted from it and the resulting signal is converted to a voltage through I/V converter 44 and applied to a 16-bit A/D converter 66 through analog switch 64. The resulting difference current is converted to 16-bit binary signal on bus 70. The 16-bit word, which is called L16C, is received through I/O circuit 20 to CPU 12, which processes this information as described hereinbelow, and the result is output from I/O circuit 24 on bus 72 to D/A converter 90, through filter 92 to a chart recorder.

In typical operation, 16-bit converter 66 requires 200 ms to do a conversion, because it is integrating during that time. 200 ms is chosen in a preferred embodiment as a multiple of 1/50 Hz and 1/60 Hz, so that any hum coming in the cell cable would be integrated out.

The 16-bit A/D 66 is also used to measure temperature. Using the same A/D 66 for temperature measurements results in increased accuracy and lower cost. In a preferred embodiment, the A/D 66 is used to measure temperature one time for each three conductivity measurement times, and hence the CPU 12 is looking at temperature once every 800 ms.

In FIG. 2, upon power up, the system software sets the I/O circuits properly, waits two seconds for the hardware to stabilize, then searches for the conductivity.

The system uses a search which allows it not to have to wait for a 200 ms A/D conversion to know whether it is too high or too low. In general, this search and find is done by first outputting a trial offset signal on bus 60, looking at the output of comparator 46 (which is hardwired to a predetermined comparison value) to see if the offset is less than or greater than the conductivity signal on lead 43, and incrementing the offset signal on bus 60 if the comparison or difference between conductivity current and offset current is less than the predetermined value.

For example, assume the conductivity signal on lead 43 is 100 $\mu$MHO. The CPU 12 first tries an offset of 0 on lead 60 and finds it is too low when the difference signal on lead 45 is connected to comparator 46.

CPU 12 then tries 5 $\mu$MHO (by incrementing the offset command) and finds it is still too low, tries 10 $\mu$MHO and finds that that, too, is still low. This process continues until the comparison of the difference value and the predetermined value (e.g., 10 $\mu$MHO) is reached. CPU 12 does this by incrementing the offset command, and finally when it tries 90 $\mu$MHO it sees a remainder of 10 $\mu$MHO (100 actual minus 90 offset). CPU 12 then waits for a 16-bit A/D conversion of 200 ms whereupon it will get the exact conductivity remainder (about 10 $\mu$MHO) on bus 70. CPU 12 knows that its offset command on bus 11 plus the L16C signal on bus 70 is equal to the actual solution conductivity.

In this way the conductivity is measured by CPU 12 with 11 bits offset plus 16 bits A/D, or 27 bits of resolution. This high resolution allows the improved conductivity detector to operate with a low level of electronics generated noise.

To further explain the operation, assume that the CPU 12 has measured the actual solution as just described. CPU 12 now has to process this information to get the value to be output to a chart recorder and the value to be shown on a front panel display. First, CPU 12 has to correct the measured conductivity to the conductivity at 25° C. (perform temperature compensation).

In FIG. 2, CPU 12 measures the solution temperature by commanding 16-bit A/D 66 to look at thermistor 80 through buffer 82 instead of the conductivity (through analog switch 64 controlled by lead 65), perform a conversion and input the 16 bits, called L16T, on bus 70 which correspond to the thermistor 80 resistance. CPU 12 then converts the value to actual temperature by using floating point mathematical operations, calculates a correction factor and applies that correction factor to the solution conductivity just measured.

By having the corrected actual conductivity, it is desirable to output this to the front panel display 30 (but not to a chart recorder). In this way the display always shows the actual conductivity (auto-ranged) and is independent of the user-commanded offset or the detector sensitivity setting. Thus the display can never go off scale. CPU 12 does this by converting the actual conductivity to BCD digits and putting that out to display 30. The same information is also output to a rear panel connector for use by an integrator or data reduction system capable of monitoring the digital output.

In order to arrive at what must be put out to the chart recorder, a user-commanded offset must be subtracted from the actual conductivity and this result scaled according to the selected sensitivity. Note that the user commanded offset is not the offset referred to earlier, but rather what the user wants to subtract from the actual conductivity to put a chart recorder output on paper.

In FIG. 2, CPU 12 subtracts this out, again utilizing floating point mathematics. Scaling is also done in floating point. This consists of multiplying the offsetted actual conductivity by a factor which depends upon the selected sensitivity settings (the higher the detector sensitivity, the larger the multiplicative factor). The final result is then converted to fixed point format and output to a 12-bit plus sign bit D/A converter 90 and then on to a chart recorder through filter 92. The output range typically is from 2.047 V.D.C. to +2.047 V.D.C.

The above description provides a basic understanding of the general process of which the improved conductivity detector processes a conductivity signal by compensating, scaling and outputting the solution conductance. It should be pointed out that CPU 12 is at the same time processing many subtasks which are desirable to assure a smooth chart recorder output, one of which is now described in more detail.

CPU 12 knows the conductivity by indirectly measuring the conductivity signal (comparing the conductivity signal on lead 43 with the offset signal on lead 63). CPU 12 does this by outputting incremental test values until the difference between the offset and conductivity signal are within a predetermined value, then measuring the precise difference between its test value and the actual conductivity. This being the case, CPU 12 follows the conductivity as it changes by changing its outputted test value on lead 60. This could tend to cause a glitch in a chart recorder output due to the unequal nature of the weights of the last significant bit (LSB) of the offset generator 62 and the most significant bit (MB) of the A/D 66.

CPU 12 is programmed to recognize and nullify this glitch before it goes to a chart recorder. The chart recorder output on bus 72 is further processed to smoothness though the detector range changes. The chart recorder output on bus 72 is therefore not a mirror image of the actual solution conductance but rather a digitally filtered image, designed to be aesthetically suitable for a user. The processing is not of such an extent as to degrade any specifications of the conductivity detector.

Another task of CPU 12 is to handle all of the diagnostics: user, test/calibration, and service. The user diagnostic is performed while the diagnostic accessory is in place on the detector rear panel. CPU 12 checks to see that a correct conductance is received by the detector, this conductance is properly temperature compensated, and that proper chart recorder output is obtained. The calibration test consists of setting up a certain output bit patterns from I/O ports so that the analog PCB may be adjusted. The diagnostics are described in more detail below.

Figure 3A:
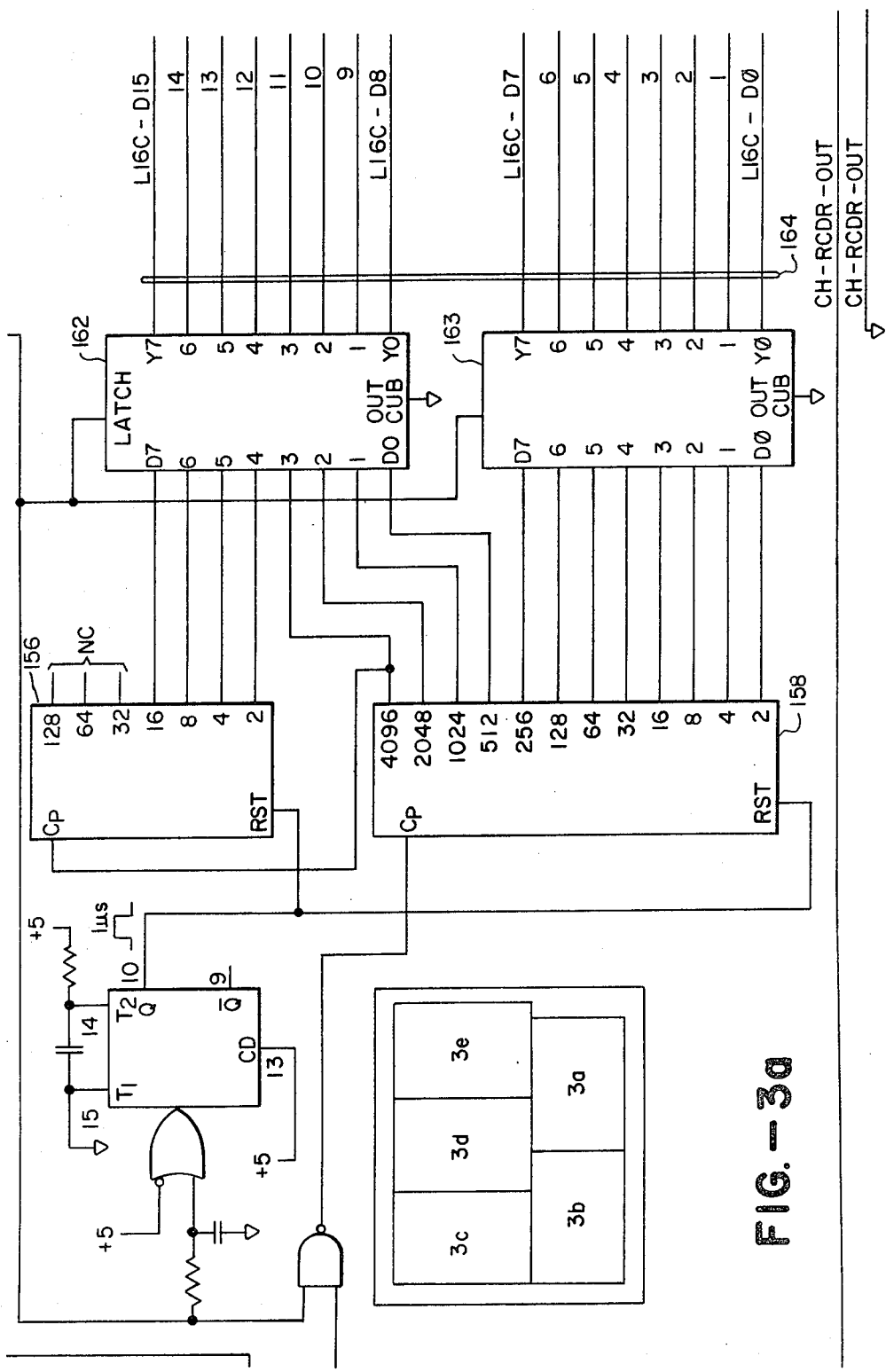
Figure 3B:
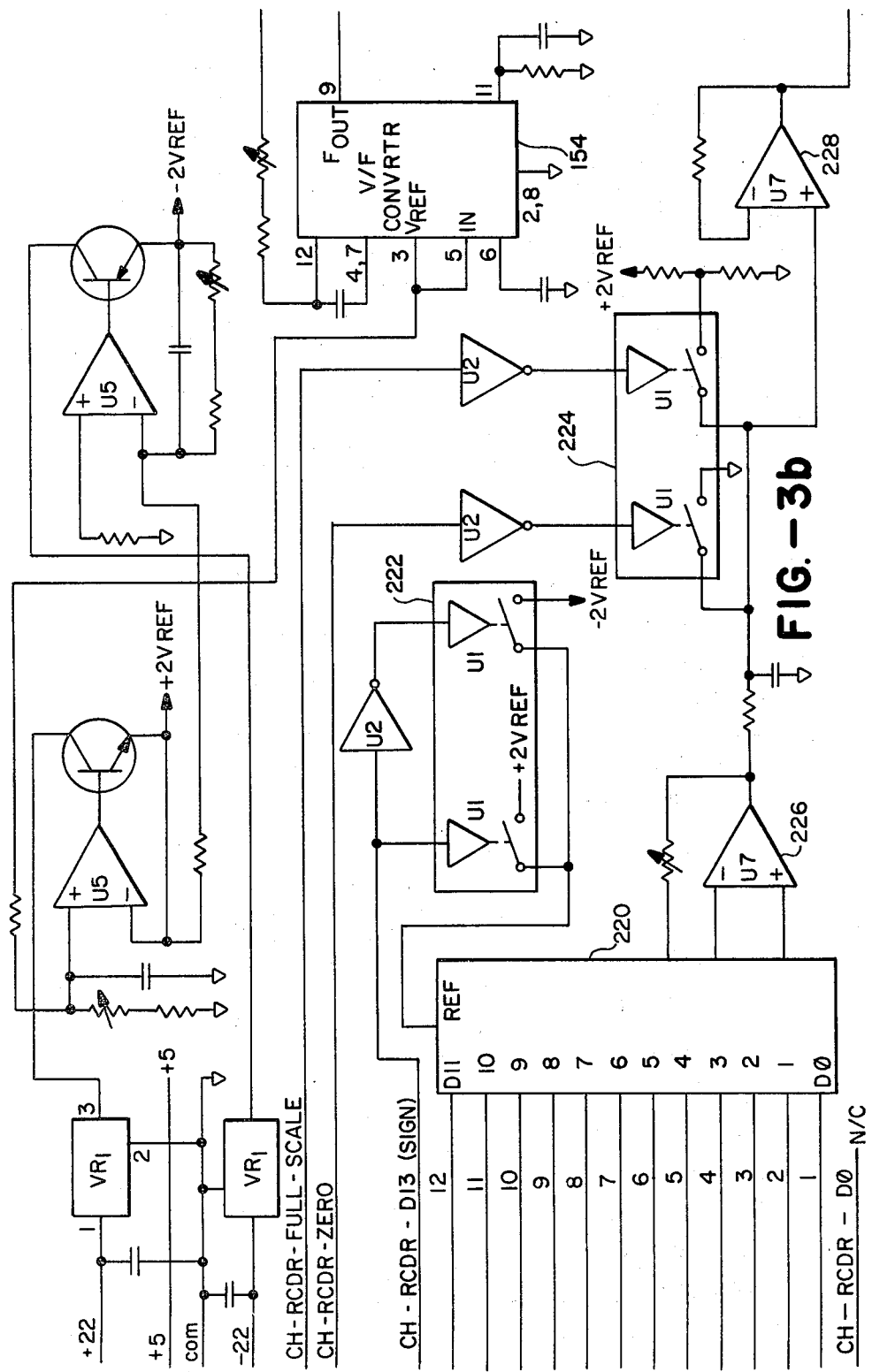
Figure 3D:
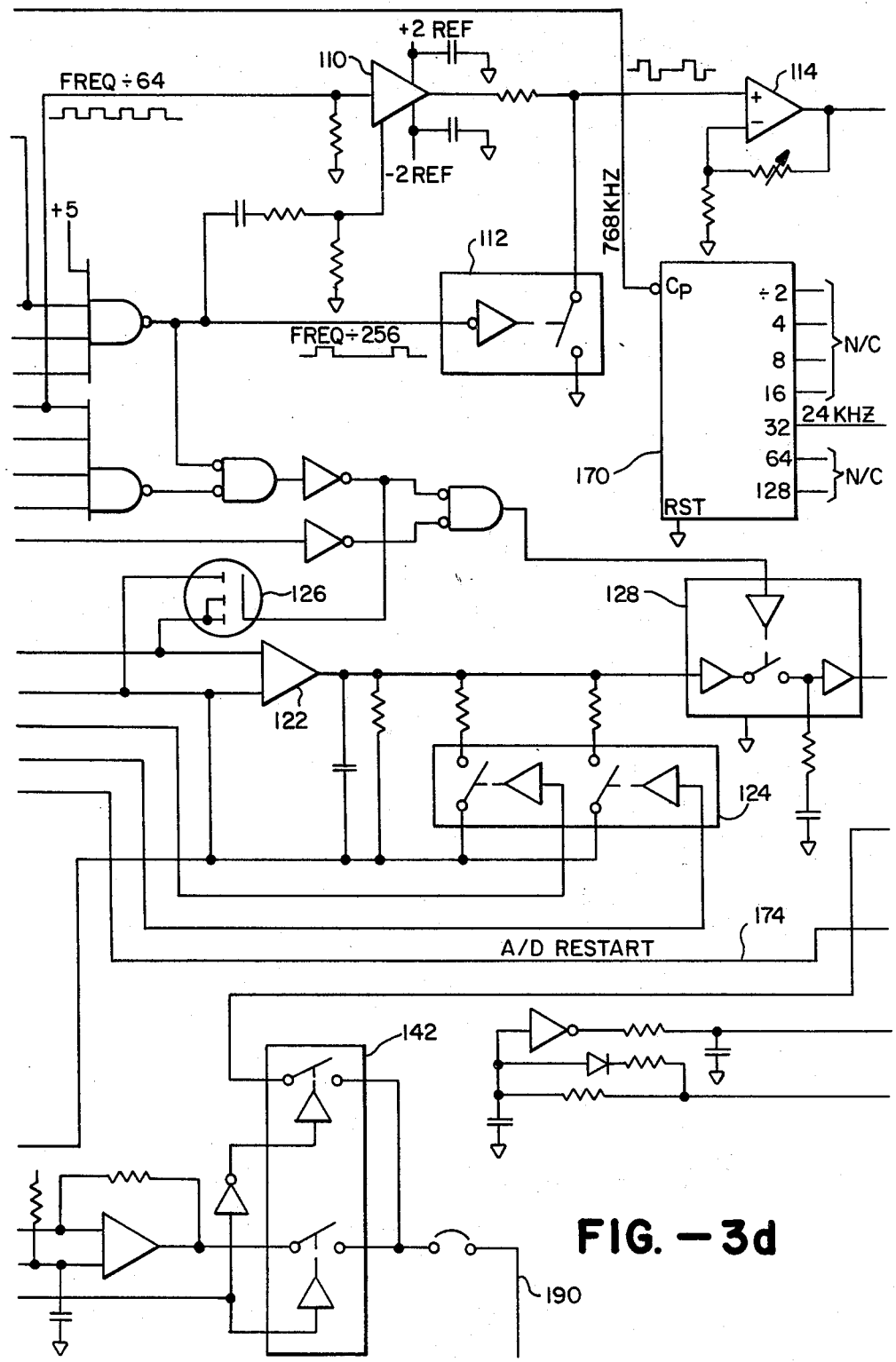

Referring now to FIG. 3 (comprising FIGS. 3A–3E, arranged as indicated), a more detailed diagram of the present invention is depicted.

In FIG. 3, the CPU 12 clock (at 3.072 MHz) on lead 101 is first divided by four in divider 102, then further divided by rate multiplier 104. The divide count is selectible by a frequency select signals on lead 105 so that CPU 12 can select cell drive frequencies of 1.5 KHz, 3 KHz or 6 KHz on 3-bit lead 105.

Divider circuit 108 is a binary divider that provides the various timing and sequencing commands, its main function being generation of the bipolar pulse waveform depicted in FIG. 1A.

In order to generate the waveform depicted in FIG. 1A, the squarewave coming in from divider 108 is gated by gates 110, 112 so that only one cycle out of every four cycles is allowed to get to cell drive amplifier 114. The squarewave is gated off by putting gate 110 in a three-state condition and turning analog switch 112 on to ground. Amplifier 114 has a user-adjustable gain so that the cell drive voltage can be set, in one embodiment, from 2.0 to 3.0 volts (peak) to allow for variations in the conductivity cell constant, and is nominally set to 2.5 volts.

The cell return line comes in on lead 120 and goes to current to voltage converter 122. The gain of converter 122 is controlled by CPU 12 and is changed by altering the digital commands through analog gate 124. In one embodiment, there are three ranges, corresponding to the ranges of the detector (0–250 $\mu$MHO, 250–2500 $\mu$MHO, 2500–10,000 $\mu$MHO). It should be noted that these ranges are strictly internal to the detector since it is auto-ranging. The cell current is measured at the very end of a bipolar pulse. In sequence, the timing logic turns off the analog switch 126 which had been keeping the cell output shorted to ground during the bipolar pulse, then samples and holds in sample/hold circuit 128 the output of current voltage converter 122. This voltage, which is proportional to the flow current, is inverted by inverter 140 and applied to a 16-bit A/D converter through analog gate 142. A limiter circuit consisting of transistor 142 and diodes 146, 148, prevent the voltage from exceeding 10 V and overloading A/D converter 150. Threshold comparator 152 provides CPU 12 with a fast indication of whether the conductivity is in the linear range of A/D 150 or not, without having to wait for the 200 ms for the A/D conversion.

In FIGS. 3A–3C, the input lead 190 to 16-bit converter is 0–10 VDC, selected to be either the conductivity or temperature signal by analog switch 142. The 16-bit A/D is an integrating type, using voltage to frequency converter 154, counters 156, 158 and latches 162, 163. Full scale input is 10 VDC, which corresponds to a frequency of 327.68 KHz out of converter 154 and a count of 65535 out of converter 150 (16 data lines 164 from latches 162, 163.

A/D timing is controlled by circuits 170–173 in the following manner. Circuits 170 and 173 divide down the 760 KHz clock frequency to induce a pulse (and an interrupt on lead 177) to CPU 12) every 200 ms at gate 175. This pulse causes the current count of counters 156, 158 to be latched into latches 162, 163. Then, counters 156, 158 are reset to begin another count typical of standard integrating A/D operation. At certain times it is desirable to short cycle converter 150 by restarting it. This is accomplished when CPU 12 outputs an A/D restart pulse which comes in on lead 174. This pulse clocks on the type-D, edge-triggered flipflop 171 which in turn restarts A/D by providing an artificial interrupt. Flipflop 171 then is reset through gate 179.

In FIG. 3, an offset generator essentially includes an 11-bit D/A converter comprising D/A converter 202 and transistors 204, 206, 208. The weighting of the least significant bit is 12.5 $\mu$A of all current which is equivalent to 5 $\mu$MHO of cell conductivity. This D/A provides a conductivity offset (by subtracting out the cell current) in the range of 0 to 10,000 $\mu$MHO.

An 8-bit D/A converter 202 provides the lower eight bits of conversion while transistors 204, 206, 208 provide the high three bits, for a total of 11 bits of resolution. Transistors 204–208 are simply on/off switches but provide a binary weighted curve out of the summing node at gate 122. The current weighting is set such that bit 0 causes a current of 12.5 $\mu$A while bit 11 causes a current of 12.8 mA to flow out of the summing node. This current is subtracted at the summing node from the conductivity cell current resulting in a difference current, which is amplified by amplifier 122. For instance, if the solution conductivity is 100 $\mu$MHO, the cell current at a cell drive of 2.5 V is 250 $\mu$A. If the offset D/A is commanded to output 250 $\mu$A (a command value of 00000001010 binary) then the resulting current amplified by amplifier 122 is zero because the cell current flows into summing node, and the offset generator D/A current flows out of the summing node down into converter 202.

In FIG. 3, CPU 12 is able to control a chart recorder through a high resolution (12-bit+sign bit) D/A, comprising converter 220 and switches 222,224. Converter 220 is standard for a current output CMOS D/A. The sign bit controls a switch which applies ±2 V to the D/A reference input. Since converter 220 is a multiplying type D/A, this serves the purpose of switching the output polarity but not the magnitude. Circuits 226, 228 convert the current output of converter 220 to a voltage. Circuit 228 provides the chart recorder zero/full scale functions, controlled from a front panel display (1.0 VDC is full scale output voltage to a chart recorder). The detector has a 100% overrange capability on this output for integrators that have a wide dynamic range.

Auto Offset

Every 200 milliseconds the detector measures conductivity and compensates for temperature differences from 25° C. The result is called "Compensated Conductivity" and is stored in the microprocessor's memory.

If the "Auto Offset" switch is "Off", another location in memory called "Conductivity Offset" is set equal to zero.

Five times a second, Conductivity Offset is subtracted from Compensated Conductivity to give a value called Offset Compensated Conductivity. Offset Compensated Conductivity will be equal to the original Compensated Conductivity if the switch is "Off".

If the switch is turned on, the value of Compensated Conductivity at that instant is stored in the value of Conductivity Offset, which is thus no longer equal to zero.

Each time a new Compensated Conductivity value has Conductivity Offset subtracted from it, the result will be value "Offset" by the value of Compensated Conductivity at the instant the switch was turned on.

The Conductivity Offset value may only be changed by turning the switch "Off" and then "On" again.

Any time one would like to know exactly what the value of Compensated Conductivity is without any subtraction of Offset, a suitable display on front panel display 30 can be provided.

The formulae for calculating the foregoing are:

$$G_{os\text{-}comp} = G_{comp} - G_{offset}$$

where $G_{os\text{-}comp}$ = Offset Compensated Conductivity $G_{comp}$ = Compensated Conductivity

| | |
|---|---|
| $G_{offset}$ = | Conductivity Offset |
| = | 0 if switch is off |
| = | Compensated Conductivity at instant switch was turned on |

Temperature Compensation

The purpose of temperature compensation is to provide a conductivity output reading which represents the conductivity of the solution at 25° C.

If the actual temperature of the solution is greater than 25° C., the conductivity measured by the detector will be higher than it would have been if the solution had been at 25° C. Thus, the detector will multiply the measured conductivity by a coefficient whose value lies between 0 and 1.

Similarly, if the actual solution temperature is less than 25° C., the measured conductivity will be raised by multiplying by a coefficient whose value is somewhat greater than 1.

The formula for calculating temperature compensation is:

$$G_{displayed} = C_t * G_{measured}$$

where $G_{displayed}$ = Final conductivity
$C_t$ = Coefficient of conversion
$G_{measured}$ = measured conductivity The coefficient may be calculated if the actual temperature and solution temperature coefficient are known. Solution temperature coefficient is a measure of how much its conductivity changes (as a percent of its conductivity at 25° C.) per degree of temperature change.

Given that $$C_t = E^{K(25-T)}$$

where $C_t$ = Coefficient of conversion
K = Solution temperature coefficient (%/°C.)
T = Actual solution temperature (°C.)

The value of K is set by the user on the detector front panel. The range typically is from 0.0%/°C. to 9.9%/°C.

The value of T is measured by the detector by means of the cell thermistor.

where $$T = \frac{K_B}{Ln(R_T/K_A)} - 273.15$$

and

T = actual temperature (°C.)
$K_A$, $K_B$ = thermistor physical constants
$R_T$ = measured thermistor resistance (ohms)

The values of $K_A, K_D$ are supplied by the thermistor manufactured and may be verified experimentally.

The value of $R_T$ is measured by means of a voltage divider network in the detector.

Software

Referring now to FIGS. 4–7, software flow charts for illustrating the operation of the conductivity detector of FIG. 2 are depicted.

In FIG. 4, after an initial power up sequence, CPU 12 of FIG. 2 initializes the I/O circuits 18–24, initializes an interrupt and clears RAM 14. Also, mathematical registers (internal to CPU 12) and the remaining hardware circuits are initialized.

The system then enters a test and function stage of the flow chart in which, if a test mode is requested, the system gets the test number requested on the front panel and executes that particular test. If test mode is no longer requested, the system initializes the hardware again and enters a find and condition routine. The first step is to determine if the offset signal generated by A/D 62 of FIG. 2 is too low, and if so the offset signal is incremented. If the offset signal is not too low, the system enables the interrupt system and enters the calculation loop, which is depicted in more detail in FIG. 5.

Referring now to FIG. 5, the calculate loop is depicted in which after the system determines that there is no test mode request, A/D error, or remote error, the system checks to see if there is a cell drive-off command. If so, the system clears the hardware. If there is no cell drive-off command, the system determines if a new temperature reading is ready, and if so the system will read the temperature compensation setting, which is normally indicated on front panel display 30 of FIG. 2. Next, the system will calculate the thermistor 80 resistance based upon the formula depicted in FIG. 5.

Next, the system will calculate the liquid temperature and the temperature correction and then exit from the loop.

In FIG. 6, the 200 ms interrupt routine is depicted in which the system first determines whether a conductivity cycle is entered, and if so loads the L16C word from the A/D converter 66 of FIG. 2. If the offset signal is low, the system adjusts the offset up, and if the offset signal is high, the system adjusts the offset signal down, as previously described. From these steps the system forms a composite sum of the offset word and L16C word.

If the system is not entering a conductivity cycle but rather a temperature cycle, the system loads the L16T word from A/D converter 62 and stores it in memory for access by the calculate loop previously described, and then the system predicts the "missing" conductivity signal.

If no temperature cycle is to be determined, and the offset has been changed as indicated, the system will then predict the "missing" composite sum conductivity.

The next step is to adjust for the offset word and multiply by the $C_T$ coefficient calculated in the calculation loop.

Finally, the system will determine if an automatic offset has been requested, and if so stores the current term in $G_{offset}$ and goes on to FIG. 7.

In FIG. 7, the offset word $G_{offset}$ is subtracted, scaled for the recorder for use in the front panel range setting, output to the chart recorder, converted to BCD format for display and output to the display and rear port.

In summary, the improved detector described above provides excellent stability because most of the signal processing is done digitally to a high degree of resolution. Most of the functions are controlled by the intructions contained within a read only memory which will allow updating of any detectors already in the field. The selectible temperature compensation constants provide for precise compensation with any eluent. Also, user diagnostics allow for rapid field servicing, and autoranging display is provided for correct conductivity display at all times.

What is claimed is:

1. An ionic conductivity detector comprising,
   means for generating a first signal representing the ionic conductivity of a solution in a conductivity cell,
   means for generating an offset signal which is applied to said first signal to generate a second signal, said second signal being maintained below a predetermined value by incrementing the offset signal, and
   means for digitally processing said offset signal and said second signal to generate a third signal representing the measured value of said conductivity.

2. A detector as in claim 1 wherein said processing means include means for generating said offset signal having an initial value, means for comparing the difference between said first and offset signals with a predetermined value, means for incrementing said offset signal if the compared signal is less than a predetermined value.

3. A detector as in claim 1 including means for displaying said measured value.

4. A detector as in claim 1 wherein said processing means include means for correcting said measured conductivity to conductivity corresponding to a predetermined temperature.

5. A detector as in claim 1 wherein said processing means include means for measuring the temperature of said solution.

6. A detector as in claim 5 wherein said processing means include means for processing the calculated temperature with predetermined temperature coefficients.

7. In an ionic conductivity detector the method comprising the steps of
   generating a first signal representing the ionic conductivity of a solution in a conductivity cell,
   generating an offset signal which is applied to said first signal to generate a second signal, said second signal being maintained below a predetermined value by incrementing the offset signal, and
   digitally processing said offset signal and said second signal to generate a third signal representing the measured value of said conductivity.

8. An ionic conductivity detector as in claim 1 wherein said means for generating a first signal include a fixed amplitude variable frequency bipolar-pulse source.

* * * * *